(12) United States Patent
Fukunaga

(10) Patent No.: US 10,426,805 B2
(45) Date of Patent: Oct. 1, 2019

(54) METHOD FOR PRODUCING LACTIC ACID BACTERIA CONTROLLING M CELLS

(71) Applicant: Hajime Fukunaga, Ube (JP)

(72) Inventor: Hajime Fukunaga, Ube (JP)

( * ) Notice: Subject to any disclaimer, the term of this patent is extended or adjusted under 35 U.S.C. 154(b) by 0 days.

(21) Appl. No.: 15/834,908

(22) Filed: Dec. 7, 2017

(65) Prior Publication Data

US 2019/0175669 A1 Jun. 13, 2019

(51) Int. Cl.
| | |
|---|---|
| *A61K 35/744* | (2015.01) |
| *A61P 31/04* | (2006.01) |
| *A61P 39/02* | (2006.01) |
| *A61P 37/08* | (2006.01) |
| *A61K 35/747* | (2015.01) |
| *C12N 5/00* | (2006.01) |

(52) U.S. Cl.
CPC .......... *A61K 35/744* (2013.01); *A61K 35/747* (2013.01); *A61P 31/04* (2018.01); *A61P 37/08* (2018.01); *A61P 39/02* (2018.01); *C12N 5/00* (2013.01)

(58) Field of Classification Search
None
See application file for complete search history.

(56) References Cited

FOREIGN PATENT DOCUMENTS

| | | |
|---|---|---|
| JP | 2008-141995 A | 6/2008 |
| JP | 5197880 B1 | 5/2013 |
| JP | 5420791 B1 | 2/2014 |
| JP | 5778325 B1 | 9/2015 |
| WO | 2012-077811 A1 | 6/2012 |

OTHER PUBLICATIONS

Juarez-Tomas et al. "Influence of pH, temperature and culture media on the growth and bacteriocin production by vaginal Lactobacillus salivarius CRL 1328" Journal of Applied Microbiology 2002, 93, 714-724 (Year: 2002).*
De Man et al. "A Medium for the Cultivation of Lactobacilli" J . Appl.Bact. 23 (I), 130-135, 1960 (Year: 1960).*
De Valdez et al. "Effect of the Rehydration Medium on the Recovery of Freeze-Dried Lactic Acid Bacteria" Applied and Environmental Microbiology, Nov. 1985, p. 1339-1341 (Year: 1985).*
Mohammad Monir Shar et al., Lactobacillus acidophilus Strain L-92 $CD4^+$ $CD25^+$ $Foxp3^+$ Regulatory T Cells and Suppresses Allergic Contact Dermatitis, Journal, Feb. 2, 2012, p. 612-616, vol. 35, No. 4, The Pharmaceutical Society of Japan, Japan.
K. Shida et al., Lactobacillus casei strain Shirota suppresses serum immunoglobulin E and immunoglobulin G1 responses and systemic anaphylaxis in a food allergy model, Journal; 2002, p. 563-570, vol. 32, The Clinical and Experimental Allergy, Blackwell Science Ltd., USA.
Toshiro Niki et al., Galectin-9 is a High Affinity IGE-Binding Lectin With Anti-Allergic Effect by Blocking IGE-Antigen Complex Formation, Journal, Sep. 23, 2009, The Journal of Biological Chemistry, The American Society for Biochemistry and Molecular Biology, Inc., USA.
S. De Kivit et al., Galectin-9 induced by dietary synbiotics is involved in suppression of allergic symptoms in mice and humans, Journal, 2002, European Journal of Allergy and Clinical Immunology, John Wiley & Sons A/S, Denmark.
Hideo Hasegawa et al., Longevity immunity and lactic acid bacteria, Journal, 2008, p. 1-8, vol. 50, No. 8, New Food Industry, Japan.

* cited by examiner

*Primary Examiner* — Thane Underdahl
(74) *Attorney, Agent, or Firm* — United IP Counselors, LLC

(57) ABSTRACT

Lactic acid bacteria according to the present invention is configured to enter M cells. The lactic acid bacteria allow galectin-9 to bind thereto by filamentation, and thus, galectin-9 which has passed through and has been expressed in the M cells binds to the filament lactic acid bacteria. Also, lactic acid bacteria (*Lactobacillus salivarius* AI-001) are provided by allowing filament lactic acid bacteria, to which galectin-9 binds, to bind to IgE antibodies so as to regulate the immunity system.

3 Claims, 7 Drawing Sheets

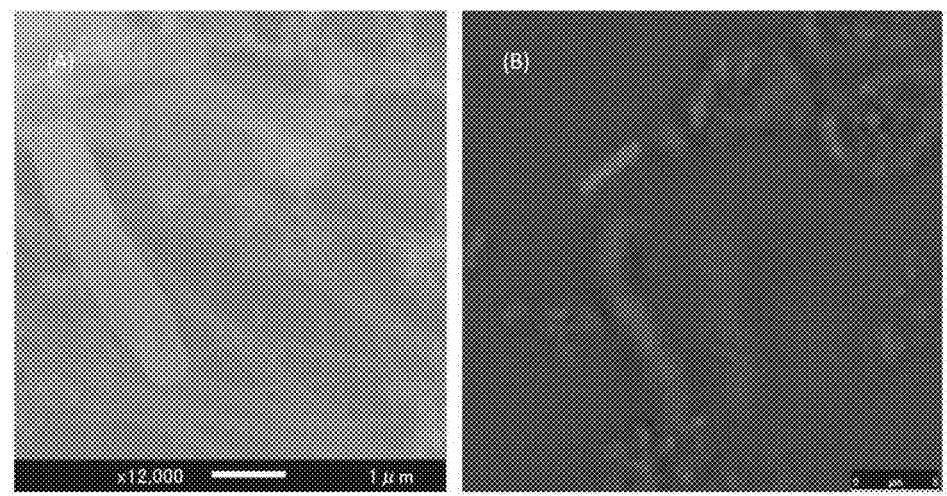
Lactobacillus salivarius (AI-001) cultured at 40°C for 30 hours (in soymilk)
FIG. 1A SEM (scanning electron microscope) photograph of AI-001.
FIG. 1B AI-001 to which galectin-9 binds photographed by confocal microscope.

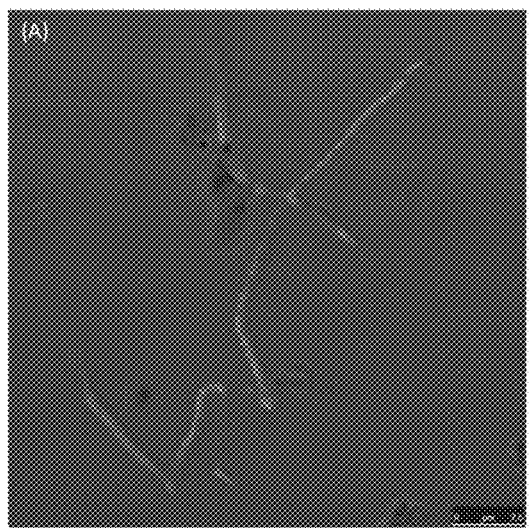
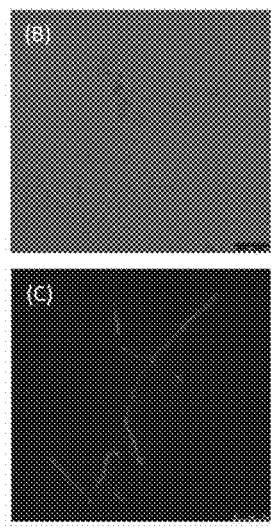
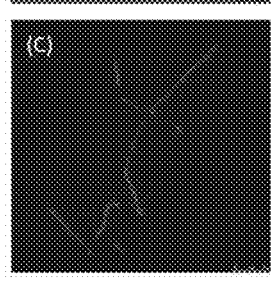
FIG. 2B
FIG. 2C
FIG. 2A
Lactobacillus casei cultured in a lactose-free MH medium at 44°C for 24 hours

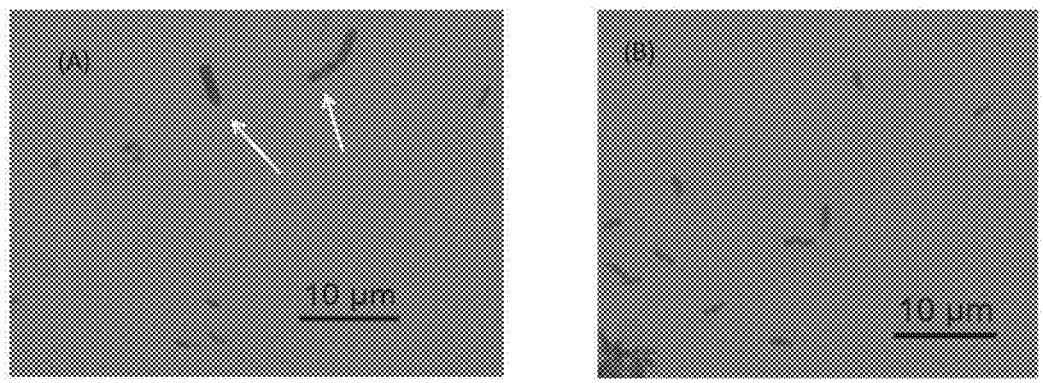
Lactobacillus salivarius (AI-001) cultured in:
FIG. 3A MH medium at 40 degrees Celsius for 30 hours
FIG. 3B MRS medium at 37 degrees Celsius for 24 hours

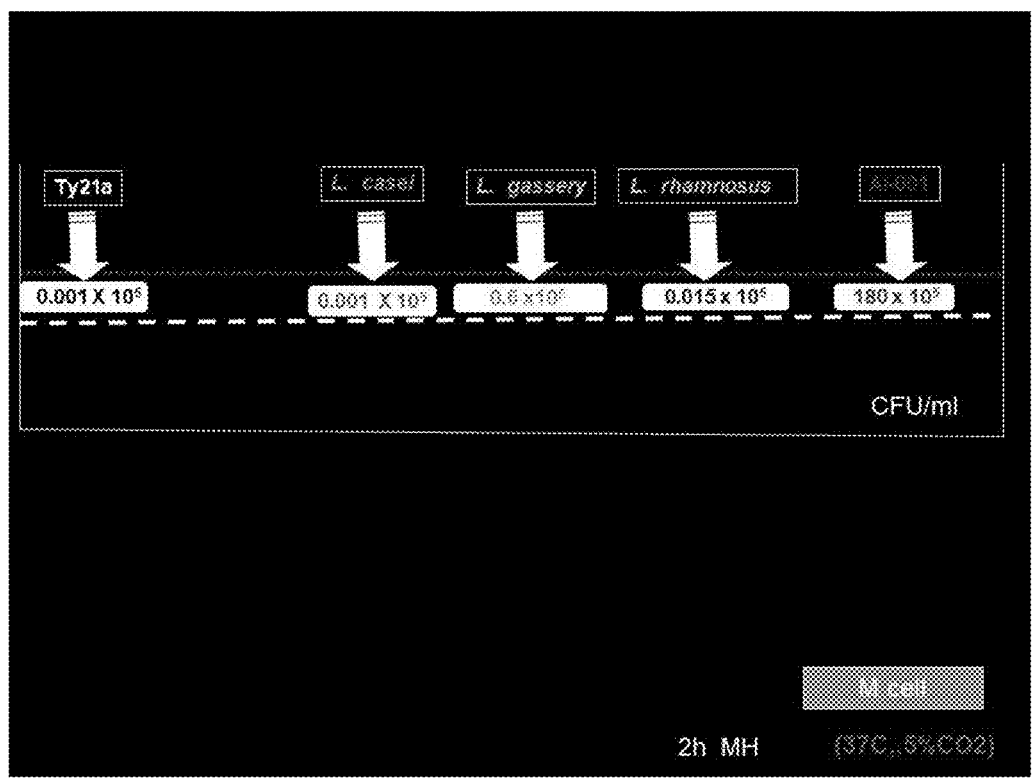
FIG. 4 Number of bacteria taken up in M cells depending on the type of lactic acid bacteria

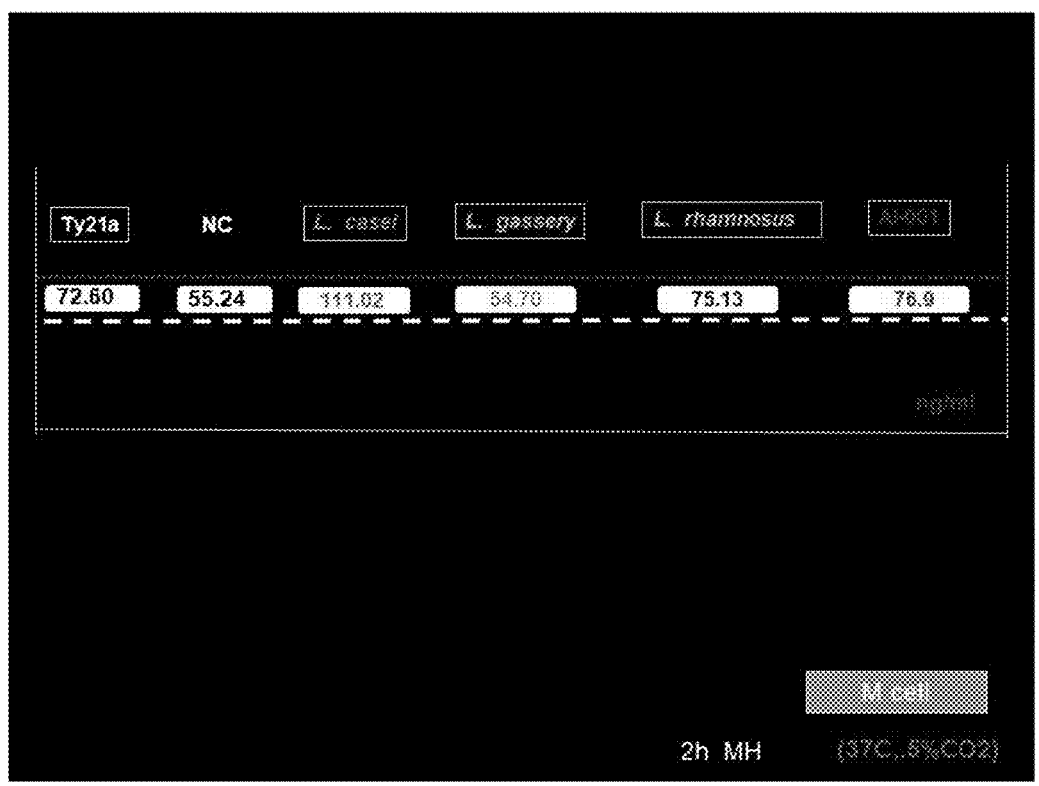
FIG. 5  Amount of TGF-β1 produced in M cells depending on the type of lactic acid bacteria

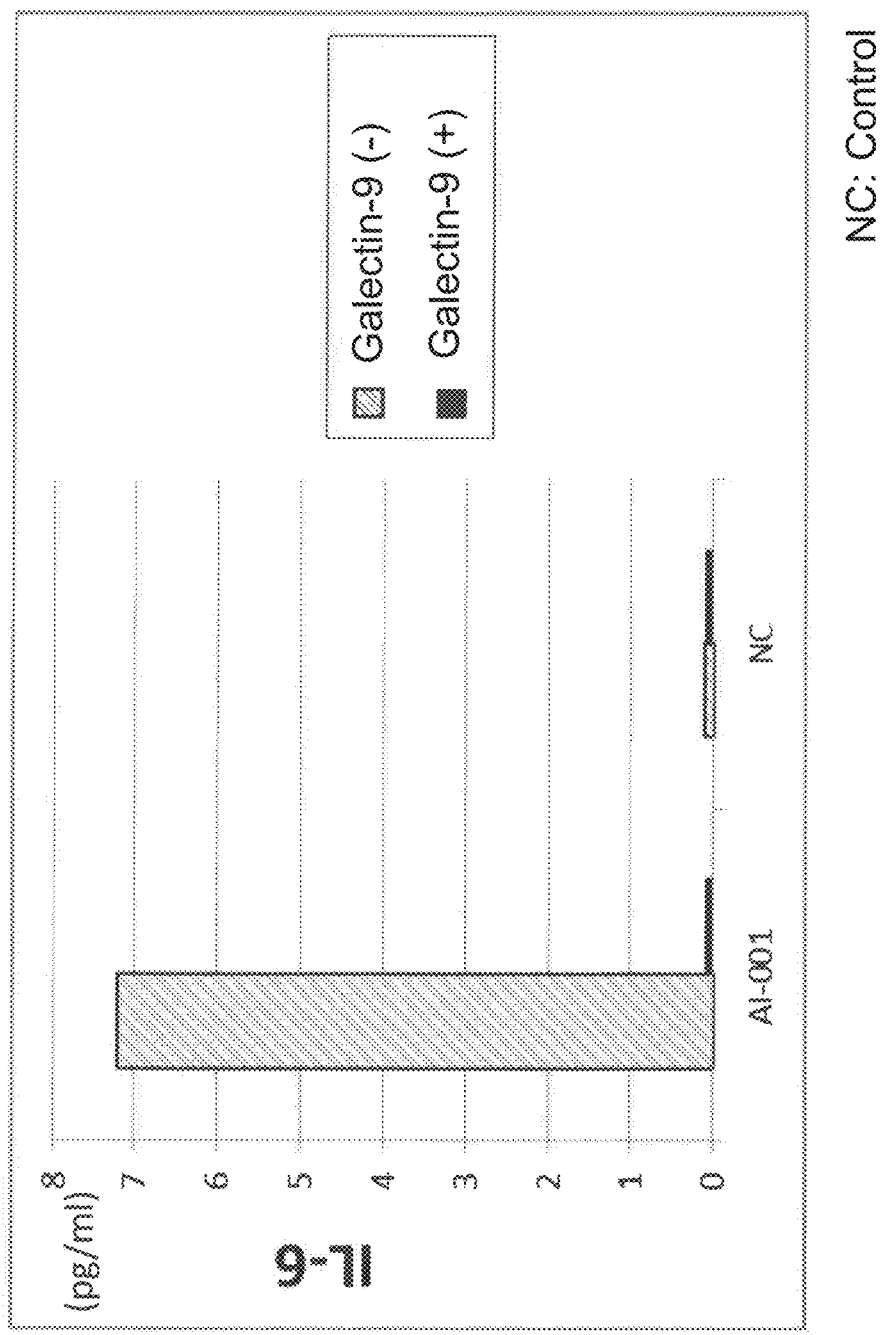
FIG. 6 Production of IL-6 from iNOS-KO macrophages depending on the type of galectin-9 binding

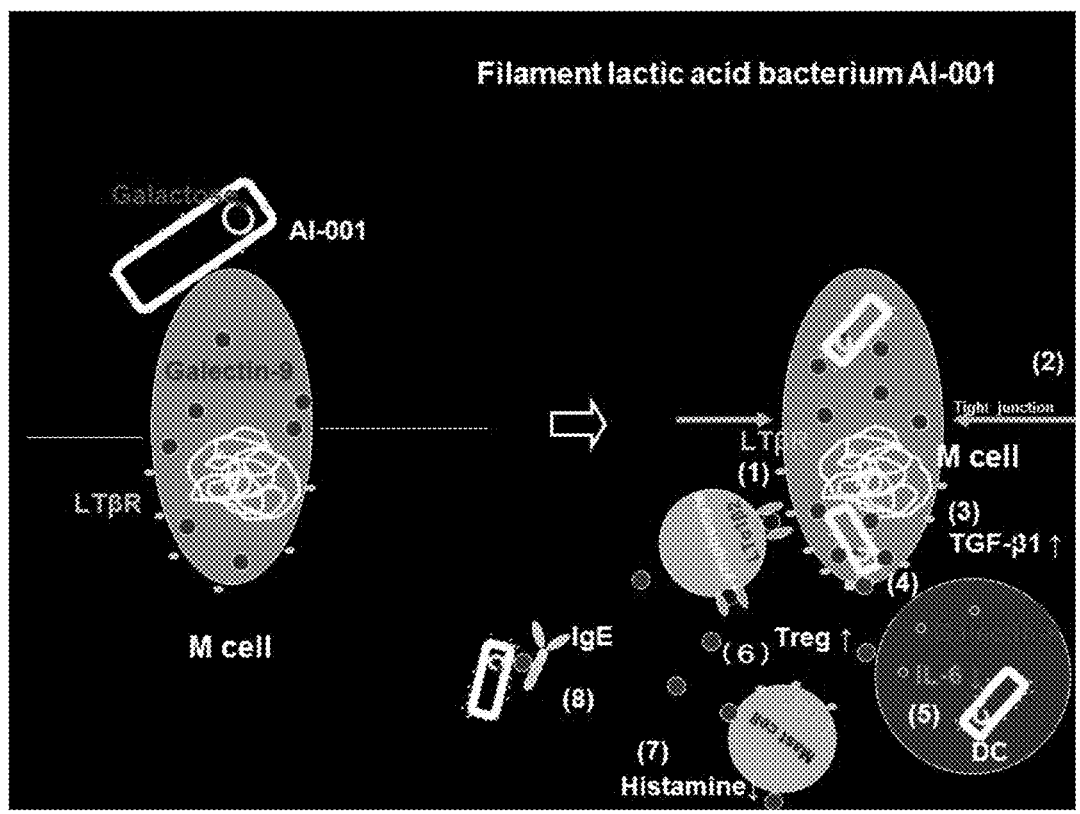
FIG. 7  Immunological functions by filament lactic acid bacterium AI-001 under M cell

METHOD FOR PRODUCING LACTIC ACID BACTERIA CONTROLLING M CELLS

CROSS-REFERENCE TO RELATED APPLICATION

The entire disclosure of Japanese Patent Application No. 2016-210203, filed on Oct. 27, 2016, is hereby incorporated herein by reference.

BACKGROUND

Technical Field

The present invention relates to lactic acid bacteria which regulate an immune function by invading into M cells.

Related Art

There are lymphoid tissues called Peyer's patches in which lymphoid nodules aggregate in a flat plate shape in the lamina propria inside the small intestine. In part of Peyer's patches where cilia are underdeveloped, there are M cells (Microfold cells) which play an important role in immunity. These M cells are considered to be part of epithelial tissues of the specially differentiated intestinal tract, and they present antigens to T cells, B cells or macrophages which are in contact with the basement membrane (basolateral) surface by taking in bacteria (antigens) through endocytosis from the intestinal lumen side.

A food allergy, which develops an excessive immune reaction to specific foods, is possibly caused by inflammation due to digested foods phagocytosed by macrophages in the M cell pocket. As an immunosuppressive mechanism which suppresses such an excessive reaction, it is considered that galectin-9 expressed in the M cells binds to an antigen taken into M cells and suppresses the immune system.

The present inventor paid attention to the relationship between galectin-9 and lactic acid bacteria, and acquired the following knowledge as a result of the experiments.

(1) Filamentous lactic acid bacteria were obtained when lactic acid bacteria were cultured at a predetermined temperature in a liquid medium without sugar such as glucose and galactose. Galectin-9 bound to the lactic acid bacteria which were changed into a filament shape.

(2) It was observed that filament lactic acid bacteria invaded (permeated) into sheet-shaped M cells in which galectin-9 was expressed.

(3) The amount of IgE in a test tube reduced when filament lactic acid bacteria to which galectin-9 bound was reacted with a prescribed amount of IgE antibodies in the test tube.

(4) Galectin-9 and GP2 were expressed in the M cells of a mouse's Peyer's patches sensitized with OVA.

(5) IgE in the blood reduced by half when filament lactic acid bacteria were orally administered to a mouse for three weeks.

Based on the above findings, the applicant proposed Patent Document 1. In Patent Document 1, cultivation in a sugar-free medium at a temperature between 37° C. and 48° C. is suggested as a method for culturing filament lactic acid bacteria bound with galectin-9 which absorbs IgE antibodies, or allergy antibodies, after passing through M cells.

In addition to Patent Document 1, Patent Documents 2 to 5 and Non-Patent Documents 1 to 4 are cited as prior art relating to M cells, galectin-9, GP 2, and IgE antibodies.

In Patent Document 2, GP2 is specifically expressed in M cells, particularly in human M cells, and it is proposed to use the GP2 as a marker for M cells.

Patent Document 3 discloses that galectin-9 acts on immune cells and has a function of suppressing excessive inflammation by controlling the immune cell to suppress the immune system.

Patent Document 4 discusses the relationship between GP2 and galectin-9, and proposes to cultivate M cells to make a sheet-shaped artificial skin based on knowledge that moving GP2 in M cells to the tight junctions exhibits a sheet-forming ability, and at the same time M cells express galectin-9 which binds to allergens and bacteria.

Patent Document 5 discloses a detoxified Salmonella (Ty21a), which is used as a vaccine strain of Salmonella bacteria. It also discloses that Salmonella (Ty21a) is a mutant (vi antigen deficiency, gal E gene mutation) of Salmonella (Ty2), and enhances the functions of M cells.

Non-Patent Document 1 reports the allergy suppressing function of lactic acid bacteria (R21).

Non-patent document 2 reports the allergy suppressing function of lactic acid bacteria (*Lactobacillus casei* strain shirota).

Non-Patent Document 3 discloses that IgE antibodies which increase in allergic diseases bind to galectin-9.

Non-Patent Document 4 discloses that galectin-9 is increased by lactic acid bacteria and oligosaccharides, and suppresses allergic reactions.

Patent Document 1: Japanese Patent No. 5778325
Patent Document 2: Japanese Patent Application Publication No. 2008-141995
Patent Document 3: International Patent Application Publication No. WO2012/077811
Patent Document 4: Japanese Patent No. 5197880
Patent Document 5: Japanese Patent No. 5420791
Non-Patent Document 1: *Lactobacillus acidophilus* strain L-92 induces CD4 (+) CD25 (+) Foxp 3 (+) regulatory T cells and suppresses allergic contact dermatitis. Mohammad Monir Shah et al. Biological and Pharmaceutical Bulletin Vol. 35 (2012) No. 4 P 612-616.
Non-Patent Document 2: *Lactobacillus casei* strain Shirota suppresses serum immunoglobulin E and immunoglobulin G1 responses and systemic anaphylaxis in a food allergy model. Shida K et al. Clin Exp Allergy. 2002 April; 32 (4): 563-70.
Non-Patent Document 3: Galectin-9 Is a High Affinity IgE-binding Lectin with Anti-allergic Effect by Blocking IgE-Antigen Complex Formation; Toshiro Niki; Shoko Tsutsui; Shigeru Hirose; Sachiko Aradono‡; Yasushi Sugimoto; Keisuke Takeshita; Nozomu Nishi and; Mitsuomi Hirashima. J Biol Chemv. 284 (47); Nov. 20, 2009
Non-Patent Document 4: Galectin-9 Induced by Dietary Synbiotics Is Involved in Suppression of Allergic Symptoms in Mice and Humans. S de Kivit, E Saeland, A D Kraneveld. Allergy. 2012; 67 (3): 343-352

A food allergy is considered to be caused if galectin-9 expressed in M cells fails to bind to digested foods. In a case where galectin-9 fails to bind to digested foods, it is assumed that binding of the tight junctions which bind M cells to each other is loose, the digested foods leak from the gap, and the digested foods without galectin-9 binding are phagocytosed by macrophages, resulting in the failure of immunosuppression.

As shown in FIG. 7, galectin-9 binds to the filament lactic acid bacteria proposed in Patent Document 1, and the IgE antibodies bind to the filament lactic acid bacteria to which galectin-9 binds so as to be induced toward the immunoregulation. However, if the filament lactic acid bacteria are too long, they cannot permeate M cells, and if they are too short, the binding of galectin-9 becomes insufficient.

In Patent Document 1, it is found that filament lactic acid bacteria that have permeated M cells are bound to galectin-9, and contribute to immunoregulation. However, filament lactic acid bacteria whose bacterial cell size is large cannot permeate M cells and do not contribute to immunoregulation.

As a result of further experiments by the present inventor, it was found that the filament lactic acid bacteria which satisfy both M cell permeation and galectin-9 binding are preferably 4 μm or greater and 10 μm or less in length. There are about 350 types of lactic acid bacteria and many of the limited lactic acid bacteria become filamentous by changing the culture conditions, but it is difficult to control their length and it is impossible to maintain the length of 4 μm or greater and 20 μm or less after culturing. In the process of becoming 20 μm, they temporarily reach 4 μm to 10 μm, but their growth cannot be stopped keeping the aforementioned length.

SUMMARY

In the present invention, *Lactobacillus salivarius* is selected as a starting lactic acid bacterium in order to culture filament lactic acid bacteria having a length in the range of 4 μm to 10 μm. This *Lactobacillus salivarius* is cultured in a lactose-free medium in an extremely limited temperature range (39° C. or higher and 41° C. or lower) for 30 hours or more (hereinafter referred to as *Lactobacillus salivarius* AI-001).

*Lactobacillus salivarius* AI-001 having a length in the range of 4 μm to 10 μm has the function of increasing the cytokine TGF-β1 from M cells and has the function of decreasing cytokine IL-6 from macrophages.

An example of a lactose-free medium includes plain soymilk. Plain soymilk in which lactic acid bacteria (*Lactobacillus salivarius* AI-001) having a length of 4 μm to 10 μm are cultured can be eaten as a yogurt-like food. It is also possible to encapsulate those cultured in plain soymilk by freeze-drying.

According to the culture method by the present inventor, *Lactobacillus salivarius* is selected as a starting lactic acid bacterium. By culturing this *Lactobacillus salivarius* in a lactose-free medium at a temperature in the range of 39° C. to 41° C. for 30 hours or more, filamentous lactic acid bacteria (*Lactobacillus salivarius* AI-001) with a length in the range of 4 μm to 10 μm suitable for M cell permeation and galectin-9 binding can be obtained.

This method uses a medium containing no lactose without using gene recombination or chemical substances, and thus, the level of safety is extremely high.

The lactic acid bacterium, *Lactobacillus salivarius* AI-001, according to the present invention enters M cells and allows galectin-9 in the M cells to bind to the surface of the cell body by oral administration. Galectin-9 binds to bacteria and digested foods, and then induces immunological tolerance. Also, galectin-9 secreted in the M cell pocket (a special structure where immune cells accumulate in the recess of M cells) binds to the IgE antibodies and becomes inactive. As a result, food allergy and atopic dermatitis are alleviated.

When the lactic acid bacteria, *Lactobacillus salivarius* AI-001, to which galectin-9 binds is phagocytized by macrophages, the production of interleukin-6 (IL-6) as an inflammatory cytokine from macrophages reduces. As a result, it is possible to create an environment, which activates immunoregulating T cells (regulatory T cells).

BRIEF DESCRIPTION OF THE DRAWINGS

Referring now to the attached drawings which form a part of this original disclosure:

FIG. 1A is an SEM (scanning electron microscope) photograph of bacterial cells when lactic acid bacteria *Lactobacillus salivarius* were cultured in a lactose-free plain soymilk at 40° C. for 30 hours and FIG. 1B is a confocal microscopic image of the bacteria cells to which galectin-9 binds.

FIG. 2A is a photograph in which a differential interference image and a fluorescent image are superimposed (galectin-9; red color), FIG. 2B is a photograph of a differential interference image only, and FIG. 2C is a photograph of a fluorescent image only (galectin-9; red color), when lactic acid bacteria *Lactobacillus casei* were cultured in a lactose-free Mueller-Hinton medium (MH) at 44° C. for 24 hours, which show that galectin-9 binds to the lactic acid bacteria in a filament shape but in a very long form (about 25 μm to 50 μm).

FIG. 3A is a photograph of the cells cultured at 40° C. for 30 hours using a Mueller-Hinton medium (MH) (lactose negative, glucose negative), and FIG. 3B is a photograph of the cells cultured at 37° C. for 24 hours using an MRS broth medium (MRS) (lactose negative, containing a high amount of glucose), to compare the size of the cells after the lactic acid bacteria *Lactobacillus salivarius* was cultured in two media and Gram-stained, in which it can be observed from the lower right scale that the length of the filament exceeds 4 μm in FIG. 3A, and filamentization of bacterial cells is not observed at a size of around 1.4 μm in FIG. 3B.

FIG. 4 is a diagram showing the number of bacteria taken into sheet-shaped M cells, the bacteria including lactic acid bacteria *Lactobacillus salivarius* AI-001, other filament lactic acid bacteria (*L. casei, L. gasser, L. rhamosus*), and salmonella vaccine strain (Ty21a) (Culture time: 2 hours).

FIG. 5 is a diagram showing the measurement results of the amount of TGF-β1 produced in M cells when lactic acid bacteria *Lactobacillus salivarius* AI-001, other filament lactic acid bacteria (*L. casei, L. gasser, L. rhamnosus*), and Salmonella vaccine strains (Ty21a) were cultured at 40° C. for 30 hours using plain soymilk (lactose-free) and were taken into the sheet-shaped M cells.

FIG. 6 shows the amount of cytokine IL-6 measured from lactic acid bacteria *Lactobacillus salivarius* AI-001 two hours after binding of galectin-9 and phagocytosis of a mouse macrophages to the *Lactobacillus salivarius* AI-001 was cultured at 40° C. for 30 hours in plain soymilk (lactose-free), in which, as a control, *Lactobacillus salivarius* AI-001 to which galectin-9 does not bind was used.

FIG. 7 is a diagram illustrating the function of filament lactic acid bacteria *Lactobacillus salivarius* AI-001.

DETAILED DESCRIPTION OF EXEMPLARY EMBODIMENTS

In order to obtain lactic acid bacteria having a size permeable to M cells with a length (4 μm or greater, 10 μm or less) suitable for galectin-9 to bind thereto, *Lactobacillus salivarius* is selected as lactic acid bacteria and this *Lactobacillus salivarius* is cultured for 30 hours or more at a temperature between 39° C. and 41° C. in a lactose-free plain soymilk as a medium. Soymilk yogurt prepared as a result of this is expected to regulate the local immune response in Peyer's patches and alleviate the symptoms of food allergy patients by suppressing the production of the inflammatory cytokine IL-6 from macrophages in food allergy patients.

Selection of Lactic Acid Bacteria

In order to isolate lactic acid bacteria contained in kumis (5 kinds of bacteria) and select lactic acid bacteria which form filaments therefrom, the culture temperature was changed from 37° C. to 48° C. Lactic acid bacteria with sizes of 4 μm or greater and 10 μm or less were selected among lactic acid bacteria whose bacteria cells were filamentized (centrifuging the cells was performed at 2400 G of centrifugal force). The selected lactic acid bacteria grew at a culture temperature of 39° C. or higher and 41° C. or lower, but could not grow at 42° C. Galectin-9 started binding to the selected lactic acid bacteria when they were cultured for 30 hours or more.

At 38° C. or lower, lactic acid bacteria of 4 μm or more could not be obtained as shown in FIG. 3B.

Identification of Lactic Acid Bacteria 1

Many commercial kits are available for distinguishing bacteria. Specifically, identification was performed using Appi 50 CHI (bioMérieux Japan Ltd., Tokyo). A kit was prepared by adding a reagent which detects substrate (sugar or protein) possibly decomposed by bacteria or detects amino acids possibly synthesized by bacteria to 50 plastic wells and drying beforehand.

The desired bacteria are inoculated into an agar medium on which they can grow, and cultivated in an incubator at 37° C. for 48 hours. Bacteria that have developed form colonies (the bacterial mass which can be confirmed by the naked eye). Some of the above colonies are scraped off with a sterile cotton swab, made into a uniform bacterial turbid solution in a 5 ml physiological saline container attached to the kit, and poured into 20 plastic wells. Since 20 plastic wells are fixed to one plastic tray, they are designed to be handled easily. This tray is cultured in an incubator at 37° C. for 18 hours. Depending on the type of the desired bacteria that are, the usage and decomposition patterns are different. Using this kit, it was estimated to be one kind of lactic acid bacteria.

Identification of Lactic Acid Bacteria 2

In order to accurately identify the lactic acid bacteria, identification was performed using the following method. DNA was extracted and purified from lactic acid bacteria *Lactobacillus salivarius* AI-001 using a DNA extraction kit (Mora gene extraction kit, AMR). To determine the 16S ribosomal RNA gene sequence used for bacterial identification, PCR was performed using a primer set of 16S common regions, and direct sequence analysis using PCR products was performed. BLAST search was performed on the obtained sequence information using the public database NCBI. As a result, the selected lactic acid bacteria were identified as *Lactobacillus salivarius*.

Binding of Galectin-9 to Lactic Acid Bacteria

Specifically, galectin-9 recombinant (R&D, USA) was dissolved in 1 ml of sterilized distilled water, and the fluorescent dye Alexa 594 was caused to bind to galectin-9 using a protein fluorescent label kit (Molecular Probes, USA). The dissolved galectin-9 solution was added in the attached fluorescent dye-containing tube, and was mixed by inverting at a room temperature for 1 hour. 500 ml of the attached buffer solution was added to this solution to obtain fluorescent dye-conjugated galectin-9. A part of the lactic acid bacteria *Lactobacillus salivarius* AI-001 cultured at 40° C. for 30 hours using a lactose-free food extract (soybean milk, grape skin crushed solution) was taken out, and adjusted to a concentration of $10^7$ CFU/ml (CFU is a unit of the number of bacteria) using sterile phosphate buffer (PBS). 20 μl of the fluorescent dye-conjugated galectin-9 is added to 1 ml of the adjusted bacterial solution and mixed by inverting at 37° C. for 1 hour. This part was placed on a collagen-fixed confocal microscope cover glass, and observed with a confocal microscope after being dried (see FIG. 1B).

Lactic Acid Bacteria *Lactobacillus salivarius* AI-001 to which Galectin-9 can Bind While the general shape of lactic acid bacteria *Lactobacillus salivarius* AI-001 is a *bacillus* having a size of around 1.4 μm as shown in FIG. 3B, it can be observed from the lower right scale in FIG. 3A that the length of the filament exceeds 4 μm when cultured at 39° C. to 41° C. for 30 hours or more.

Detection of Lactic Acid Bacteria Phagocytosed by M Cells and Macrophages

Next, regarding lactic acid bacteria phagocytosed by M cells and macrophages according to the present invention, *Lactobacillus salivarius* AI-001, other lactic acid bacteria, and a *Salmmonella* vaccine strain (Ty21) as a negative control were compared. Sheet-shaped M cells, iNOS-KO mouse macrophages and BALB/C mouse macrophages were used for the experiments. These sheet-shaped M cells were developed by the present inventor. An iNOS-KO mouse is a typhoid *bacillus* infection model mouse, and a BALB/C mouse was prepared as a control. Both were prepared according to the following procedure.

First, M cells were cultured on a Transwell™ filter. The concentration of the M cells was adjusted to $8 \times 10^5$ cell/ml, and the cell solution was added to the Transwell™ filter at a ratio of 2 ml to 4 cm² of the culture vessel. The cell culture solution containing 20% Fetal bovine serum was added to the upper and lower layers. On the fourth day, the cell culture solution in the upper and lower layers was exchanged for a new solution. On the next fourth day, the cell culture solution was exchanged again. Two days later, it was confirmed that the M cells have increased to cover the whole surface of the filter. When the M cells spread to the entire culture vessel, the cell culture solution in the upper and lower layers was replaced with a cell culture liquid without serum components, and 20 μm of anti-LTPR antibody was added to the lower layer. The stimulation of anti-LTβR antibody moved intracellular GP2 to the intercellular adhesion sites (tight junctions), and strengthened the binding between cells. The culture solution was exchanged two days later, and the cell culture solution was exchanged every two days thereafter, and six days later, the M cell sheet was completed.

The following method was performed in order to quantify the number of bacteria which had invaded the M cells. 50 μl of the bacterial solution was added, and was left to stand in an incubator with 5% carbon dioxide gas at 37° C. for 2 hours. The upper and lower layers of each well of Transwell™ were washed three times with a cell culture solution without serum components which was heated to 37° C., and excessive bacteria that had been added was removed. Next, a solution concentration of 250 μg/ml antibiotic gentamicin was prepared with a cell culture solution free of serum components, 2 ml each was added to the upper and lower layers of Transwell™, and was allowed to stand in an incubator at 37° C. with 5% carbon dioxide gas for two hours.

By performing the above method, excessive bacteria around the M cells are sterilized, and the only lactic acid bacteria which have entered the M cells can be detected. Antibiotic gentamicin is characterized by that it is not taken into cells. By using this character of antibiotic gentamicin, the cell invading bacteria can be detected quantitatively.

After two hours, gentamicin around the cells was washed three times with sterile PBS. In order to take out living bacteria in cells, bacteria were collected by lysing M cells with a 0.1% solution of a surfactant Triton-X 100. A dilution series was prepared with sterile PBS, and inoculated into an MRS agar medium. This was left to stand in an incubator with 5% carbon dioxide gas at 37° C. for 48 hours. By counting colonies of growing bacteria, the number of bacteria which had entered the M cells was detected quantitatively with the dilution ratio being taken into account.

Detection of Lactic Acid Bacteria which have Passed Through M Cell Sheet

An M cell sheet formed on the Transwell™ filter was prepared. Electrical resistance was measured using an intercellular resistance measuring device (Millicell; Millipore) in order to confirm that there was no gap in the sheet. By confirming that the electric resistance value was 200 $\Omega \cdot cm^2$ or more, it was determined that there was no gap in the sheet. Bacteria were added from the upper layer of Transwell™ on which the M cell sheet was formed. Two hours after the bacteria were added, the culture solution in the lower layer of Transwell™ was collected. The number of lactic acid bacteria contained in the collected liquid was counted. At the same time, after 24 hours of inoculation with lactic acid bacteria, the electric resistance of the M cell sheet was measured again and no change was confirmed. From this observation, it was concluded that the detected lactic acid bacteria had passed through the M cells.

Lactic acid bacteria *Lactobacillus salivarius* AI-001, and the *Salmonella* vaccine strain (Ty21a) used as a negative control, were adjusted to $10^7$ CFU/ml, and 50 μl of the bacteria solution of each was added to the upper layer of a well where another M cell sheet was formed, and was left to stand in an incubator with 5% carbon dioxide gas at 37° C. The culture solution in the lower layer was collected with a sterile pipette. A dilution series was prepared with sterile PBS and inoculated into an MRS agar medium. This was cultured in a thermostatic incubator at 37° C. for 48 hours. By counting colonies of growing bacteria, the number of bacteria which had passed through was detected quantitatively with the dilution ratio being taken into account.

Detection of Lactic Acid Bacteria Phagocytosed by Macrophages and Measurements of Cytokine The following method was performed in order to quantify the number of bacteria phagocytosed by macrophages. As macrophages, macrophages of an iNOS-KO mouse which is a typhoid *bacillus* infection model and macrophages of a BALB/C mouse were used. Removal of macrophages from the abdominal cavity of the mice was performed in accordance with Lissner et al. (J Immunol 131: 3006-3013).

Macrophages removed from the mice were added to six well plates (Corning), and left to stand in an incubator with 5% carbon dioxide gas at 37° C. for 4 days. The upper and lower layers of each well were washed three times with a cell culture solution without serum components which had been heated to 37° C., inoculated with bacteria (lactic acid bacteria AI-001, and Ty21a as a control), and cultured for two hours. Two hours later, in order to remove excessive bacteria, each well was washed three times with a cell culture solution without serum components which had been heated to 37° C. Next, 2 ml of a cell culture solution without serum components containing antibiotic gentamicin 250 μg/ml was added to each of six well plates, and was left to stand in an incubator at 37° C. with 5% carbon dioxide gas for two hours.

By performing the above method, excessive bacteria around the macrophages are sterilized, and the only bacteria which have entered the macrophages can be detected. Antibiotic gentamicin is characterized by that it is not taken into cells. By using this character of antibiotic gentamicin, the bacteria which have been taken into the macrophages can be detected quantitatively.

Two hours later, gentamicin around the cells was washed three times with sterile PBS. In order to take out living bacteria from the cells, bacteria were collected by lysing M cells with a 0.1% solution of a surfactant Triton-X 100. A dilution series was prepared with sterile PBS, and inoculated into an MRS agar medium. This was cultured in an incubator with 5% carbon dioxide gas at 37° C. for 48 hours. By counting colonies of growing bacteria, the number of bacteria which had entered the macrophages was detected quantitatively with the dilution ratio being taken into account.

Cytokines produced from macrophages which haven taken *Lactobacillus salivarius* AI-001 to which galectin-9 binds (galectin-9 (+)), and cytokines produced from macrophages which have taken *Lactobaciullus salivarius* AI-001 to which galectin-9 does not bind (galectin-9 (−)) were measured. Bacteria cells of *Lactobacillus salivarius* AI-001 to which galectin-9 binds were cultured in soymilk at 40° C. for 30 hours (as a control, bacteria cells cultured in an MRS medium at 37° C. for 24 hours), added with 20 μl of recombinant Galectin-9 (R&D), left to stand at room temperature for one hour, and added to the plate on which macrophages had developed ($10^5$ CFU/ml). By culturing for two hours, a cell lysate was created according to the method described above. A protease inhibitor cocktail (Sigma) was added to this cell lysate at a ratio of 1/100, and using 50 μl of this mixture, IL-6 was measured with an ELISA kit (R&D). See FIG. 6. As shown in FIG. 6, galectin-9-bound *Lactobacillus salivarius* AI-001 (galectin-9 (+)) cultured in soymilk was able to reduce the production of the cytokine IL-6 ($p<0.01$).

The above is summarized in FIG. 7. On the surface of the bacterial cells of *Lactobacillus salivarius* AI-001 of the present invention, a sugar chain (galactose polymer) to which galectin-9 binds is expressed, and thus it is taken up a lot in M cells by binding to the galectin-9 on the surface of the M cells.

(1) LTβR is expressed on the M cells which have taken *Lactobacillus salivarius* AI-001, and activated lymphocytes which are an activated ligand thereof bind.

(2) Tight junctions are strengthened by this combined stimulation.

(3) The production of TGF-β increases in the M cells.

(4) *Lactobacillus salivarius* AI-001 in the M cells, to which galectin-9 binds, is discharged from the M cells into an M cell pocket.

(5) *Lactobacillus salivarius* AI-001, to which galectin-9 binds, is phagocytosed by macrophages or DC, and suppresses the production of IL-6.

(6) Regulatory T cells (Treg) are activated by the increase in production of TGF-β and the suppression of production of IL-6.

(7) Activated Treg cells suppress histamine release from mast cells.

(8) Galectin-9 binding *Lactobacillus salivarius* AI-001 binds to IgE antibody which is an allergic antibody.

Lactic acid bacteria *Lactobacillus salivarius* AI-001 according to the present invention can be utilized for producing TGF-β1 by being taken in by M cells in large quantities, and for reducing the production of interleukin-6 (IL-6), which is an inflammatory cytokine from macrophages, by allowing galectin-9 to bind to the cell bodies. Therefore, lactic acid bacteria *Lactobacillus salivarius* AI-001 can be developed as health-promoting food and medicine with an effect of regulating allergy and inflammation such as a food allergy and atopic dermatitis.

General Interpretation of Terms

In understanding the scope of the present invention, the term "comprising" and its derivatives, as used herein, are intended to be open ended terms that specify the presence of the stated features, elements, components, groups, integers, and/or steps, but do not exclude the presence of other unstated features, elements, components, groups, integers and/or steps. The foregoing also applies to words having similar meanings such as the terms, "including", "having" and their derivatives. Also, the terms "part," "section," "portion," "member" or "element" when used in the singular can have the dual meaning of a single part or a plurality of parts. Finally, terms of degree such as "substantially", "about" and "approximately" as used herein mean a reasonable amount of deviation of the modified term such that the end result is not significantly changed. For example, these terms can be construed as including a deviation of at least ±5% of the modified term if this deviation would not negate the meaning of the word it modifies.

While only selected embodiments have been chosen to illustrate the present invention, it will be apparent to those skilled in the art from this disclosure that various changes and modifications can be made herein without departing from the scope of the invention as defined in the appended claims. Furthermore, the foregoing descriptions of the embodiments according to the present invention are provided for illustration only, and not for the purpose of limiting the invention as defined by the appended claims and their equivalents.

What is claimed is:

1. A method for producing lactic acid bacteria, *Lactobacillus salivarius*, having a filament form with a length in a range of 4 μm to 10 μm to control M cells, comprising:
   selecting *Lactobacillus salivarius* as a starting material; and
   culturing the *Lactobacillus salivarius* in a lactose-free medium at a temperature in a range of 39° C. to 41° C.

2. The method for producing lactic acid bacteria according to claim 1, wherein the lactic acid bacteria increase cytokine TGF-β1 from M cells.

3. The method of producing lactic acid bacteria according to claim 1, wherein the lactic acid bacteria reduce cytokine IL-6 from macrophages by causing galectin-9 to bind to the lactic acid bacteria.

* * * * *